(12) United States Patent
Mahony et al.

(10) Patent No.: US 7,691,048 B2
(45) Date of Patent: Apr. 6, 2010

(54) INCUBATOR PATIENT HEALTH CARE SYSTEM

(75) Inventors: Michael Joseph Mahony, Schenectady, NY (US); Daniel White Sexton, Niskayuna, NY (US); John Erik Hershey, Ballston Lake, NY (US); John Carter, Jr., Houston, TX (US); Howard Leigh Krain, Summit, NJ (US)

(73) Assignee: General Electric Company, Niskayuna, NY (US)

( * ) Notice: Subject to any disclaimer, the term of this patent is extended or adjusted under 35 U.S.C. 154(b) by 474 days.

(21) Appl. No.: 10/955,294

(22) Filed: Sep. 30, 2004

(65) Prior Publication Data

US 2005/0215845 A1    Sep. 29, 2005

Related U.S. Application Data

(60) Provisional application No. 60/555,543, filed on Mar. 23, 2004.

(51) Int. Cl.
*A61G 11/00* (2006.01)

(52) U.S. Cl. ........................................................ 600/22

(58) Field of Classification Search ............. 600/21–22, 600/483, 529, 549; 128/903; 5/655
See application file for complete search history.

(56) References Cited

U.S. PATENT DOCUMENTS

| 6,409,654 | B1 | 6/2002 | McLain ........................ 600/22 |
| 6,416,471 | B1 * | 7/2002 | Kumar et al. ................ 600/300 |
| 6,648,820 | B1 * | 11/2003 | Sarel .......................... 600/300 |
| 6,679,830 | B2 | 1/2004 | Kolarovic et al. ............. 600/22 |
| 6,852,085 | B2 * | 2/2005 | Rubinstein ................... 600/549 |
| 2002/0044059 | A1 * | 4/2002 | Reeder et al. ............. 340/573.1 |
| 2002/0196141 | A1 * | 12/2002 | Boone et al. ................ 340/540 |
| 2004/0147818 | A1 * | 7/2004 | Levy et al. .................. 600/300 |
| 2005/0085687 | A1 * | 4/2005 | Mackin et al. ................ 600/22 |

* cited by examiner

*Primary Examiner*—Charles A Marmor, II
*Assistant Examiner*—Christine D Hopkins
(74) *Attorney, Agent, or Firm*—Patrick K. Patnode

(57) ABSTRACT

An infant monitoring system includes an incubation chamber configured to house an infant. Furthermore, the infant monitoring system includes a data reception interface configured to receive a wireless signal indicative of a vital sign. The infant monitoring system may be configured to communicate wirelessly with a LAN or a remote monitoring system.

11 Claims, 3 Drawing Sheets

US 7,691,048 B2

INCUBATOR PATIENT HEALTH CARE SYSTEM

CROSS REFERENCE TO RELATED APPLICATIONS

This application claims the benefit of U.S. Provisional Application No. 60/555,543 filed on Mar. 23, 2004, which is incorporated herein in its entirety by reference.

BACKGROUND

The invention relates generally to an incubator system, such as for premature infants, that monitors the infant and its environment.

Over the years, a number of devices have been developed for caring for an infant in a hospital care environment. As will be appreciated by one skilled in the art, one of the best-known devices for infant care, such as of a premature infant or an otherwise delicate or sick infant, is an incubator. The incubator is utilized to provide an infant a controlled environment, wherein the environment within the incubator, such as, for example, the temperature, humidity, and oxygen content, may be monitored and controlled.

The vital signs of the infant in the incubator, for example, temperature, respiration rate, pulse, and other physiological parameters, may be monitored via sensors to evaluate the condition of the infant. For example, a temperature of the infant in the incubator may be monitored via a transducer, such as a temperature sensor, that may be attached to the infant. However, the attachment of the transducer to the infant may disadvantageously lead to several limitations such as the inadvertent detachment of the sensor by infant movement, and may also limit the movement of the infant. Additionally, the leads employed to attach the various transducers to the infant may cause bruising of the tender skin of the infant in the incubator. Furthermore, the length of the lead wires may interfere with a caregiver providing timely critical care to the infant. In addition, if the leads wires are long, the lead wires may get dirty or contaminated, such as by being dragged on the floor, and may thereby lead to unhygienic conditions for the infant.

It would be desirable to reduce the number and length of lead wires used in infant monitoring. Furthermore, it may be desirable to develop a technique that efficiently monitors the vital signs of the infant in the incubator.

SUMMARY

Briefly, in accordance with an exemplary embodiment of the present technique, an infant monitoring system is provided. The infant monitoring system includes an incubation chamber configured to house an infant. Furthermore, the infant monitoring system includes a data reception interface configured to receive a wireless signal indicative of a vital sign of the infant.

According to a further embodiment of the present technique, an infant monitoring system is provided. The infant monitoring system includes an incubation chamber configured to house an infant. Furthermore, the infant monitoring system includes a data reception interface configured to receive a wireless signal indicative of a vital sign of the infant, wherein the wireless signal comprises one of a radio frequency signal, an infrared signal, an ultrasonic signal, an optical signal or an acoustic signal. In addition, the infant monitoring system includes a sensor unit configured to generate and transmit the wireless signal.

In accordance with another embodiment of the present technique, a sensing and transmitting unit is provided. The sensing and transmitting unit includes a sensing component configured to measure an infant vital sign. Additionally, the sensing and transmitting unit includes a data analysis component configured to analyze the infant vital sign to generate a set of analyzed data. Furthermore, the sensing and transmitting unit includes a transmitting component configured to transmit a wireless signal indicative of the set of analyzed data.

According to another embodiment of the present technique, a method for monitoring an infant is presented. The method includes measuring an infant vital sign. The method includes wirelessly transmitting the infant vital sign to a data reception interface of an incubator.

In accordance with a further embodiment of the present technique, a method of manufacturing an infant monitoring system is presented. The method includes providing an incubation chamber configured to house an infant. Furthermore, the method includes providing a data reception interface configured to receive a wireless signal transmitted from within the incubation chamber.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION OF EXEMPLARY EMBODIMENTS

In providing care for an infant, particularly a premature newborn, it is generally desirable to continuously monitor one or more infant vital signs, such as temperature, blood pressure, cardiac activity, and/or blood oxygen level. It is also desirable to transmit signals indicative of the infant vital sign data to a monitoring station, such as a local monitor, a central monitoring station located in a hospital or a remote monitoring station. The techniques discussed herein address some or all of these issues.

Figure 1:
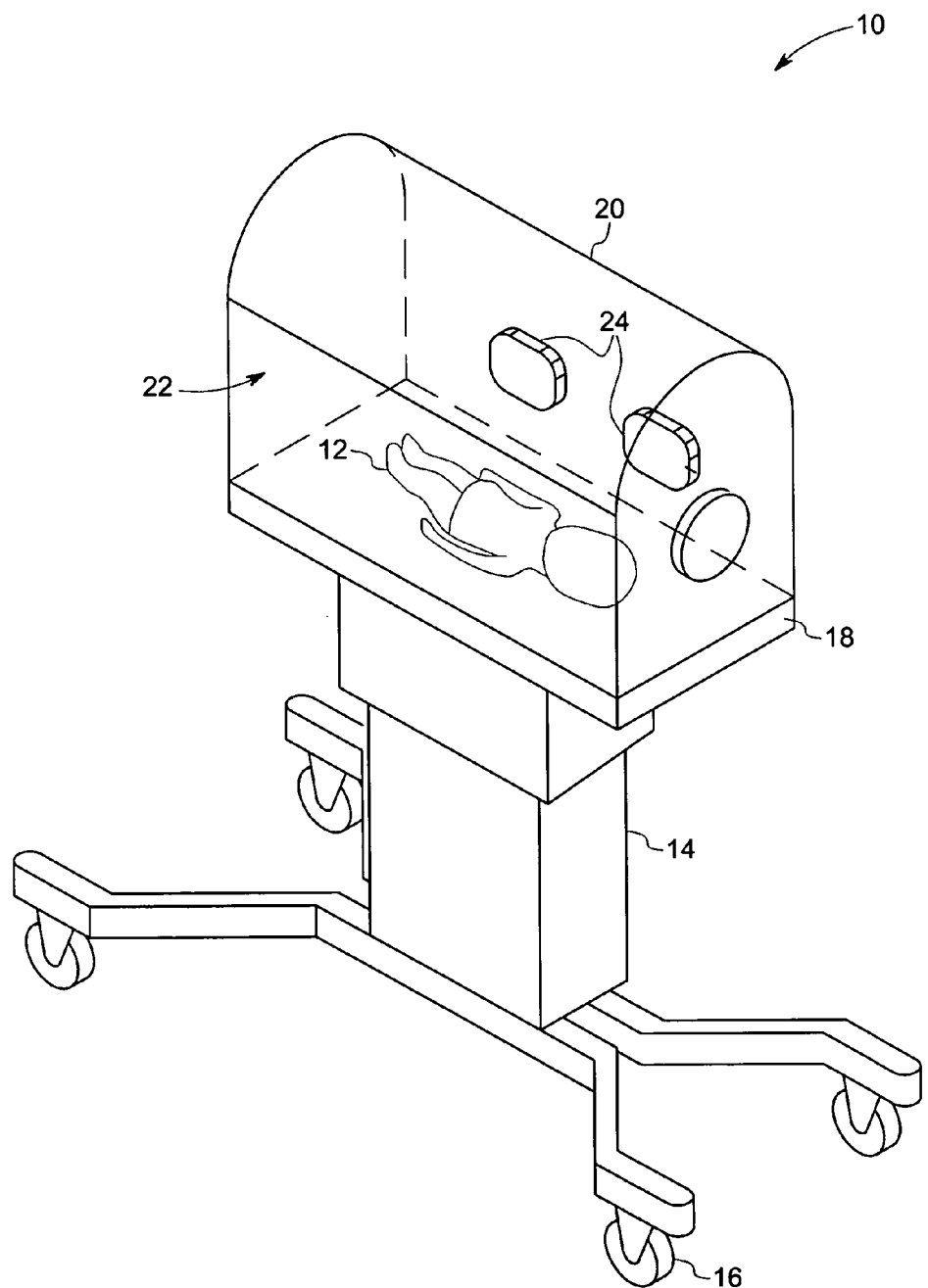
FIG. 1 is a perspective view of an incubator.

Referring to FIG. 1, an incubator 10 configured to house an infant 12, such as a premature infant, is illustrated. Typically, the incubator 10 includes a base 14, generally mounted on a series of rollers 16. In addition, a support plate 18 may be mounted on the base 14, wherein the support plate 18 may be configured to support an infant 12. The incubator 10 may also include a hood 20 mounted on the base 14 to form an incubation chamber 22, wherein the incubation chamber 22 may be configured to provide a controlled environment isolated from the surrounding environment.

Furthermore, the hood 20 may include access portals 24 to facilitate access to the infant 12 without significantly altering the controlled environment within the incubation chamber 22. Also, one or more sensors (not shown) may be disposed on the infant 12. As will be appreciated by one skilled in the art, the one or more sensors may be configured to measure physiological parameters, such as vital signs of the infant 12. For example, the vital signs of the infant 12 may include a temperature, a pulse, an electrocardiogram, or a blood oxygen level.

Figure 2:
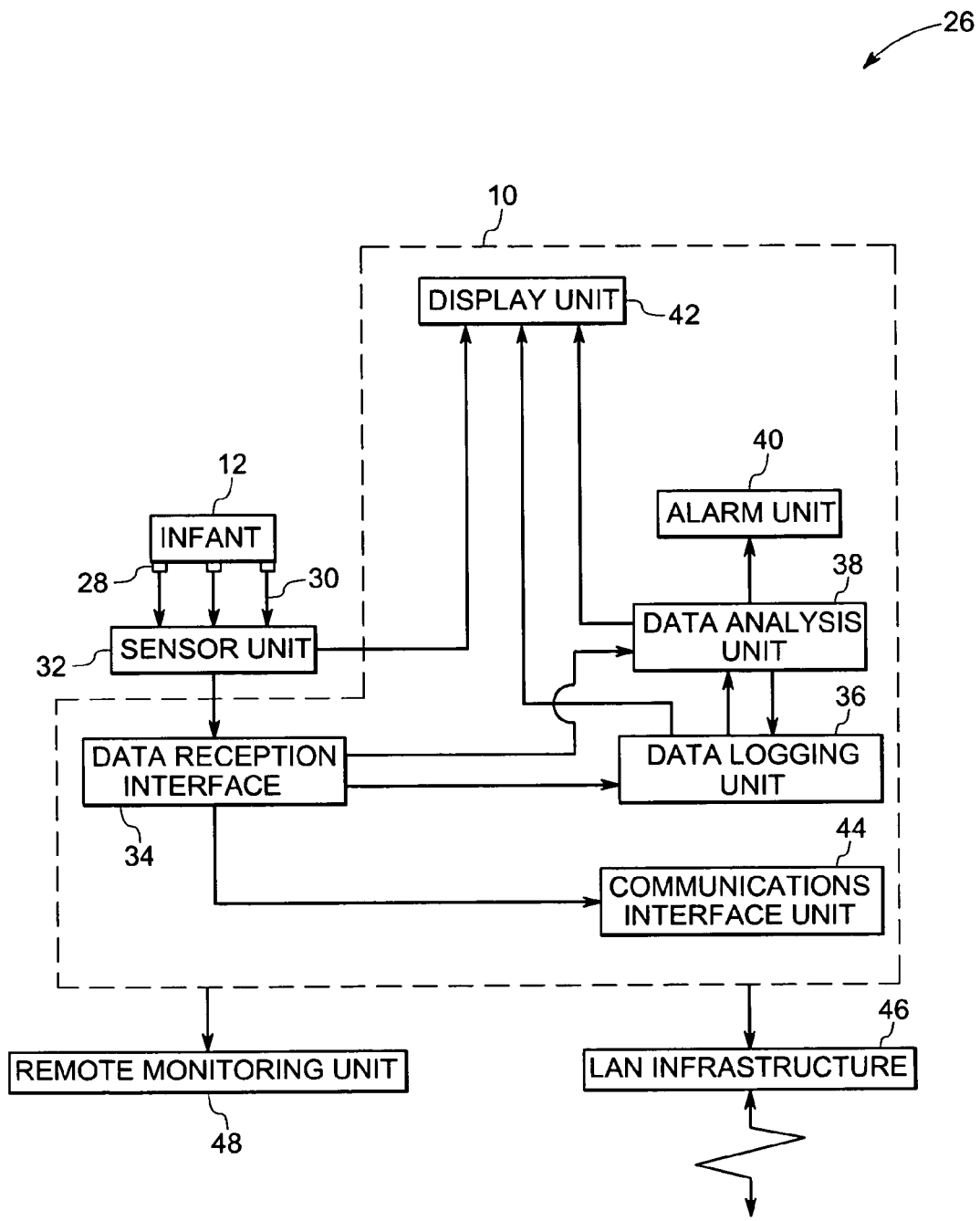
FIG. 2 is a diagrammatic illustration of an infant monitoring system in accordance with an exemplary embodiment of the present technique.

Referring to FIG. 2, a block diagram depicting an infant monitoring system 26 in accordance with an exemplary embodiment of the present technique is illustrated. As previously mentioned, one or more sensors 28 may be disposed on the infant 12. In an exemplary embodiment of the present technique, one or more leads 30 facilitates the measurement of infant vital signs from the sensors 28 disposed on the infant 12 by a sensor unit 32. The sensor unit 32 may be configured to measure the vital signs via at least one sensor 28 coupled to the sensor unit 32 by the one or more leads 30. Furthermore, the sensor unit 32 may be configured to generate and transmit a wireless signal indicative of the vital signs. In accordance with this exemplary embodiment, the sensor unit 32 may be disposed in close proximity to the infant 12. Because the sensor unit 32 is situated close to the infant 12, the lead wires 30 employed to couple the sensors 28 to the sensor unit 32 may be short. For example, in accordance with an exemplary embodiment of the present technique, the length of the lead wires 30 may be 12 inches or less. Further, in accordance with another embodiment of the present technique, the length of the lead wires 30 may be 18 inches or less. The short lead wires 30 may facilitate providing care to the infant 12 in a timely fashion due to their relative unobtrusiveness. Additionally, the short lead wires 30 may also allow the infant 12 to be taken out of the incubator 10 (see FIG. 1) relatively effortlessly in order to assist with parent infant interaction. As illustrated in FIG. 2, the leads 30 may be coupled to the sensor unit 32. The sensor unit 32 will be described hereinafter with reference to FIGS. 3 and 4. While the lead wires 30, including short lead wires, may be used in some embodiments of the present technique, other embodiments may use wireless techniques, such as infrared transmission, radio frequency transmission, ultrasonic transmission, optical transmission or acoustic transmission for providing infant vital sign data from the sensors 28 to the sensor unit 32.

The sensor unit 32 may communicate with a data reception interface 34 configured to receive the wireless signal indicative of the vital sign. The wireless signal may communicate raw sensor data of vital signs obtained by sensors on the infant 12, such as temperature, blood pressure, electrocardiogram data, or blood oxygen level. In another embodiment of the present technique, however, the wireless signal may include processed sensor data, such as mean or median measurements, alarm indicators, or filtered data or measurements. According to one embodiment of the present technique, the wireless signal may include one of an infrared signal, a radio frequency signal, an ultrasonic signal, an optical signal or an acoustic signal.

Furthermore, the infant monitoring system 26 may include a data logging unit 36 configured to communicate with the data reception interface 34. The data logging unit 36 may be configured to log data received from the sensor unit 32, such as raw or processed vital sign measurements. For example, the data logging unit 36 may be configured to log the temperature of the infant 12 over a predetermined period of time. Further, the data logging unit 36 may also be configured to log infant vital sign data that has been processed via a data analysis unit, which will be described hereinafter.

Additionally, the infant monitoring system 26 may include a data analysis unit 38 that may be coupled to the data logging unit 36 and/or the data reception interface 34. The data analysis unit 38 may be employed to aid in the analysis of the sensed data transmitted by the sensor unit 32. For example, the data analysis unit 38 may facilitate the analysis of infant vital sign data to ensure that one or more of the measured infant vital signs are within a predetermined range. However, if one or more of the infant vital signs exceed a predetermined threshold value, an alarm may be sounded to alert the caregiver. In particular, an alarm unit 40 or circuit may be coupled to the data analysis unit 38 to trigger an alarm if the infant vital sign exceeds the predetermined threshold value. Based upon an analysis of the measured infant temperature data by the data analysis unit 38, if the temperature value lies outside the predetermined range of temperature, the alarm unit 40 sounds an alarm to alert the caregiver. Alternatively, the data analysis unit 38 may be employed to analyze infant vital sign data that has been logged by the data logging unit 36. In other words, the data analysis unit 38 may be employed to facilitate the analysis of currently measured data or previously logged data.

Further, the infant monitoring system 26 may include a display unit 42 that may be coupled to the data analysis unit 38, the data logging unit 36 and/or the data reception interface 34 to display currently measured, logged or analyzed infant vital signs. Currently, in existing caregiving environments, display monitors are configured to display infant temperature data. Furthermore, as will be appreciated by one skilled in the art, separate stand-alone monitors are currently employed to display other infant vital sign data, such as electrocardiogram data, blood pressure or blood oxygen level. According to aspects of the present technique, the display unit 42 may be configured to advantageously display some or all of the measured signals and/or data indicative of the infant vital signs simultaneously.

As illustrated in FIG. 2, the infant monitoring system 26 may also include a communications interface unit 44. The communications interface unit 44 is configured to communicate, via wires or wirelessly, with a public or proprietary network. For example, the communications interface unit 44, in one embodiment, communicates with a wireless local area network (LAN) of a hospital or medical facility. In another embodiment, the communications interface unit 44 communicates with a public network, such as the Internet, such as over a cellular or wireless interface. For example, in this embodiment, the communications interface unit 44 may communicate with a web server or other site which may be accessible remotely by an interested party. Furthermore, the communications interface unit 44 may comprise one end a point-to-point communications system. In addition, the communications interface unit 44 may include or implement additional features, such as encryption and authentication, for use in communication.

In one embodiment, the communications interface unit 44 is configured to aid in the wireless communication of infant vital sign data to a public or proprietary network, such as to a central server or web located in a medical facility. For example in the depicted embodiment, the communications interface unit 44 allows wireless communication with a LAN infrastructure 46, such as may be found in a hospital. Such wireless communication may include the use of infrared, radio frequency, ultrasonic, optical or acoustic signals. The vital sign data, once received by the LAN infrastructure 46, may then be communicated to a caregiver, such as a physician, and/or to the family of the infant 12 via a wired or wireless medium.

Additionally, the infant monitoring system 26 may include a remote monitoring unit 48, such as a remote display, a console, or a workstation, that may be configured to receive the wireless signal indicative of vital sign data. The remote monitoring unit 48 may facilitate a caregiver, such as a physician, to access infant vital sign data from a remote location, which may advantageously assist the caregiver in remotely monitoring the infant 12. Alternatively, the infant vital sign data may be transmitted via the wireless medium to a central monitoring system that may be located within the caregiving facility. A caregiver or doctor may then access the central monitoring system to remotely view the infant vital sign data.

Figure 3:
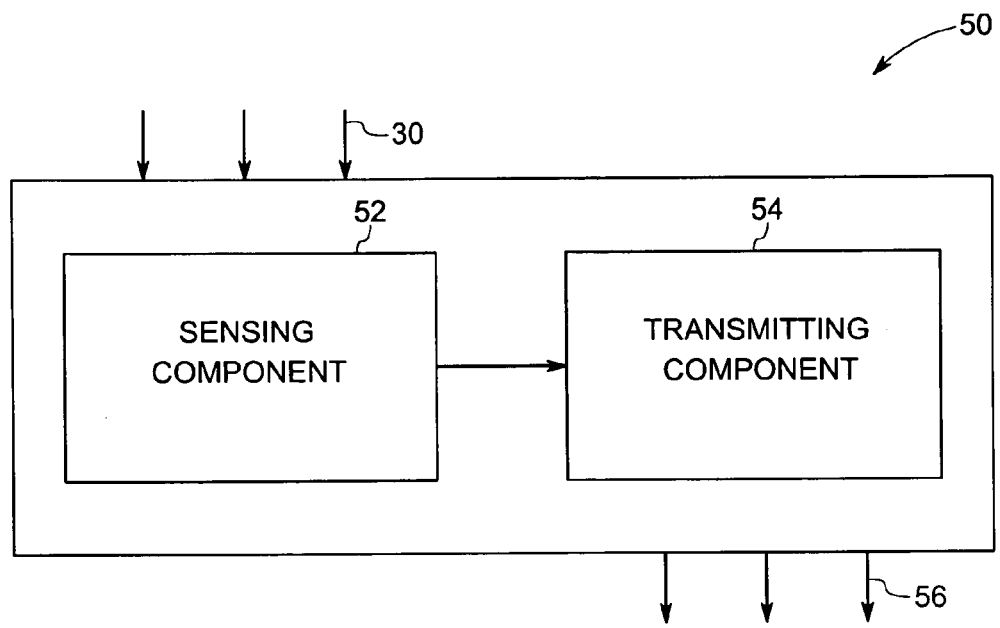
FIG. 3 is a diagrammatic illustration of the sensor unit of the infant monitoring system of FIG. 2 according to aspects of the present technique.

Turning now to FIG. 3, there is shown an exemplary sensor unit 50. In accordance with aspects of the present technique, the exemplary sensor unit 50 facilitates the measurement and transmission of the measured infant vital sign data. As depicted in FIG. 3, the sensor unit 50 may include a sensing component 52. The sensing component 52 may be configured to readout or measure the infant vital sign data via at least one sensor 28 (see FIG. 2) coupled to sensing component 52 via one or more sensing leads 30. Alternatively, the sensing component 52 may be coupled to the at least one sensor 28 wirelessly.

Additionally, the sensor unit 50 may include a transmitting component 54 configured to transmit a wireless signal 56 indicative of the infant vital sign data. In one exemplary embodiment, the wireless signal 56 may include one of an infrared signal, a radio frequency signal, an ultrasonic signal, an optical signal or an acoustic signal.

In accordance with one aspect of the present technique, the transmitting component 54 may be adapted to transmit the wireless signal 56 indicative of the infant vital sign data to the data reception interface 34 (see FIG. 2). Furthermore, the transmitting component 54 may also be configured to transmit the wireless signal 56 indicative of the infant vital sign data to be displayed on the display unit 42 (see FIG. 2). Moreover, in accordance with an exemplary aspect of the present technique, infant vital sign data measured via the sensor unit 50 may be transmitted from the sensor unit 50 to the data reception interface 34 from different locations relative to the data reception interface 34, such as from within or without the incubator 10 (see FIG. 2). Similarly, in one embodiment, the sensor unit 50 may transmit to different data reception interfaces as the sensor unit 50, and infant 12 (see FIG. 2), are moved relative to the different data reception interfaces. For example, in one implementation, the sensor unit 50 transmits the wireless signal 56 indicative of the measured sensor data to the nearest data reception interface, enabling the continuous monitoring of the infant 12 when the infant 12 is moved between rooms or incubators.

Figure 4:
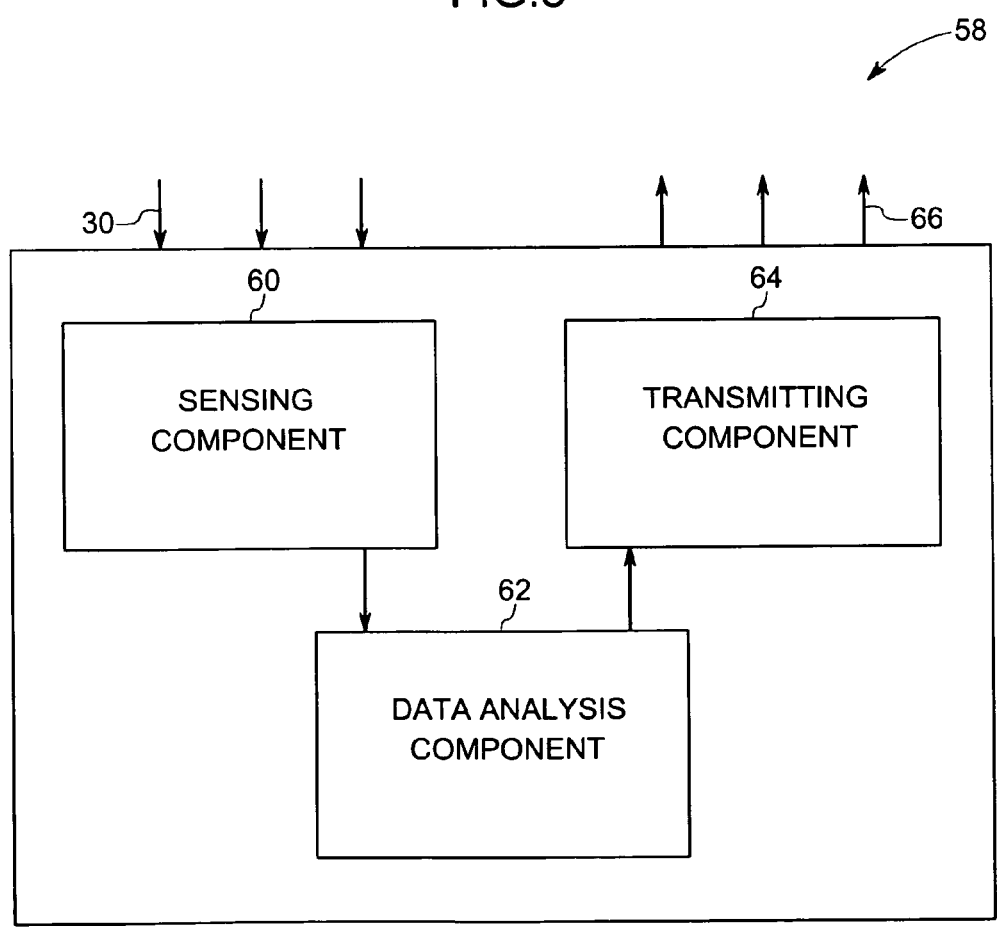
FIG. 4 is a diagrammatic illustration of the sensor unit including data analysis circuitry according to further aspects of the present technique.

FIG. 4 illustrates another exemplary sensor unit 58. In accordance with further aspects of the present technique, the exemplary sensor unit 58 facilitates the acquisition and processing of the measured sensor data prior to transmission to the data reception interface 34 (see FIG. 2). As illustrated in FIG. 4, the sensor unit 58 may include a sensing component 60. The sensing component 60 may be configured to facilitate the measurement of infant vital sign data as described hereinabove with reference to FIG. 3.

As exemplified in FIG. 4, the sensor unit 58 may also include a data analysis component 62. The data analysis component 62 may be configured to analyze the infant vital sign data to generate a set of analyzed data. For example, the analysis of the infant vital sign data may include an amplification, a filtering, an analysis, or some other processing of the infant vital sign data. In accordance with one embodiment of the present technique, the processed signal may include a filtered signal. In accordance with another embodiment of the present technique, the processed signal may include an alarm signal that may be generated in response to the infant vital sign exceeding a predetermined threshold value.

In addition, the sensor unit 58 may also include a transmitting component 64. As described hereinabove with reference to FIG. 3, the transmitting component 64 may be configured to transmit a wireless signal 66 indicative of the analyzed data generated by the data analysis unit 62 to the data reception interface 34. In accordance with aspects of the present technique, the wireless signal 66 may include one of a filtered signal or an alarm signal generated by the data analysis component 62.

While only certain features of the invention have been illustrated and described herein, many modifications and changes will occur to those skilled in the art. Further, as will be appreciated by one skilled in the art, other patients such as elderly patients and patients in the intensive care unit (ICU), may also benefit from the continuous monitoring of the one or more of vital signs employing the techniques described hereinabove. It is, therefore, to be understood that the appended claims are intended to cover all such modifications and changes as fall within the true spirit of the invention.

The invention claimed is:

1. An infant monitoring system, comprising:
 a data sensing component, comprising:
  one or more sensors configured to be placed on an infant;
  a sensor unit in wireless communication with the one or more sensors, wherein
 the sensor unit is configured to measure one or more physiological parameters based on signals received from the one or more sensors, the sensor unit comprising a transmitter configured to wirelessly transmit the one or more physiological parameters or data derived from the one or more physiological parameters; and
 an incubator, comprising:
  a data reception interface configured to wirelessly receive the one or more physiological parameters or derived data.

2. The infant monitoring system of claim 1, further comprising a display unit configured to display the one or more physiological parameters or derived data.

3. The infant monitoring system of claim 1, further comprising a data logging unit configured to log the one or more physiological parameters or derived data.

4. The infant monitoring system of claim 1, further comprising a data analyzing unit configured to analyze the one or more physiological parameters or derived data.

5. The infant monitoring system of claim 1, wherein the one or more physiological parameters comprise one of a temperature, a blood pressure, an electrocardiogram, or a blood oxygen level.

6. The infant monitoring system of claim 1, further comprising an alarm unit configured to trigger an alarm in response to the one or more physiological parameters exceeding a predetermined threshold value.

7. The system of claim 1, wherein the transmitter configured to wirelessly transmit comprises the transmitter configured to transmit one of a radio frequency signal, an infrared signal, an ultrasonic signal, an optical signal or an acoustic signal.

8. The system of claim 1, wherein the incubator is configured to communicate with at least one of a remote monitoring unit or a local area network.

9. The system of claim 1, further comprising a remote monitoring unit configured to receive the physiological parameters or data derived from the one or more physiological parameters.

10. The infant monitoring system of claim 1, wherein the data analysis component is configured to analyze the one or more physiological parameters or derived data by at least amplifying or filtering the one or more physiological parameters.

11. The infant monitoring system of claim 1, further comprising a wired sensor unit connected to the one or more sensors by one or more lead wires eighteen inches in length or less, wherein the wired sensor unit is configured to measure one or more physiological parameters based on signals received from the one or more sensors via the lead wires.

* * * * *